(12) United States Patent
Besselink

(10) Patent No.: US 6,669,718 B2
(45) Date of Patent: Dec. 30, 2003

(54) APPARATUS AND METHOD FOR PLACING BIFURCATED STENTS

(76) Inventor: Petrus Besselink, Gronausestraat 1220, Enschede 7534 (NL)

( * ) Notice: Subject to any disclaimer, the term of this patent is extended or adjusted under 35 U.S.C. 154(b) by 175 days.

(21) Appl. No.: 09/908,446

(22) Filed: Jul. 18, 2001

(65) Prior Publication Data

US 2002/0077692 A1 Jun. 20, 2002

Related U.S. Application Data

(60) Provisional application No. 60/166,274, filed on Nov. 18, 1999.

(30) Foreign Application Priority Data

Nov. 17, 2000 (WO) .................................. PCT/IB00/01831

(51) Int. Cl.[7] ........................... A61F 2/06; A61M 29/00
(52) U.S. Cl. ........................................ 623/1.11; 606/194
(58) Field of Search ................................ 606/191, 192, 606/194, 195; 623/1.11, 1.12, 1.23, 1.35; 600/585

(56) References Cited

U.S. PATENT DOCUMENTS

| | | | |
|---|---|---|---|
| 5,613,980 A | * | 3/1997 | Chauhan ..................... 606/194 |
| 5,720,735 A | | 2/1998 | Dorros |
| 6,099,497 A | * | 8/2000 | Adams et al. ............... 606/194 |
| 6,129,738 A | | 10/2000 | Lashinski et al. |
| 6,132,459 A | | 10/2000 | Piplani et al. |
| 6,187,036 B1 | | 2/2001 | Shaolian et al. |
| 6,261,316 B1 | | 7/2001 | Shaolian et al. |
| 6,287,277 B1 | * | 9/2001 | Yan ............................. 606/194 |

* cited by examiner

Primary Examiner—Michael J. Milano
Assistant Examiner—Jessica R Baxter
(74) Attorney, Agent, or Firm—Dinsmore & Shohl LLP

(57) ABSTRACT

An apparatus and method to place a bifurcated stent into a body lumen by using a delivery device requiring only one incision. Relative axial movements between a catheter and a sheath in the delivery device permit the insertion and expansion of the stent. During placement into and removal from the patient's body, the branch sections of the bifurcated stent are held in substantially parallel arrangement. Opposing tendencies between a self-expanding stent and leg portions within the delivery device can be tailored such that, during deployment, the bifurcation bias due to the elastic spring forces in the stent overcome the parallel bias within the delivery device. In situations where a balloon-expandable stent is used, the delivery device obviates the need for balloon change during stent placement. Such catheters can also be used for angioplasty, eventually in combination with stenting, and are also equally applicable to both multibranch and side branch body lumens, which are difficult to reach with conventional devices and techniques.

24 Claims, 9 Drawing Sheets

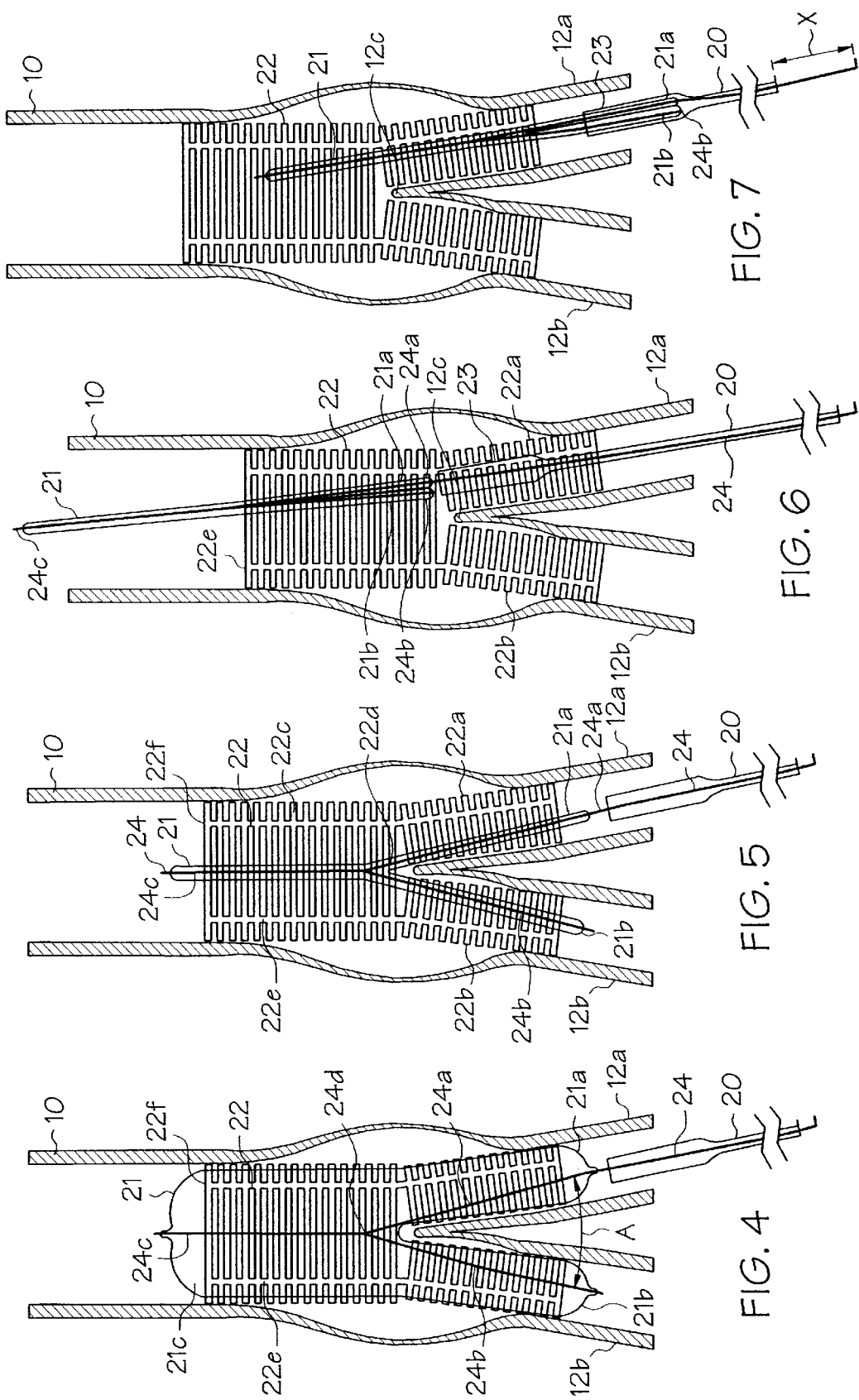

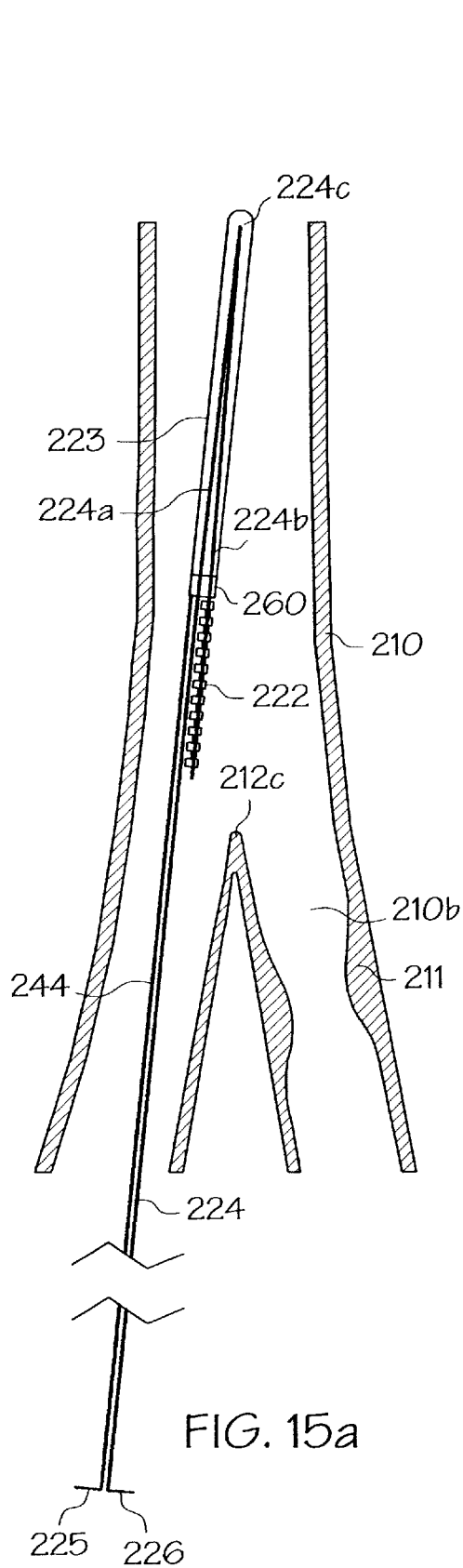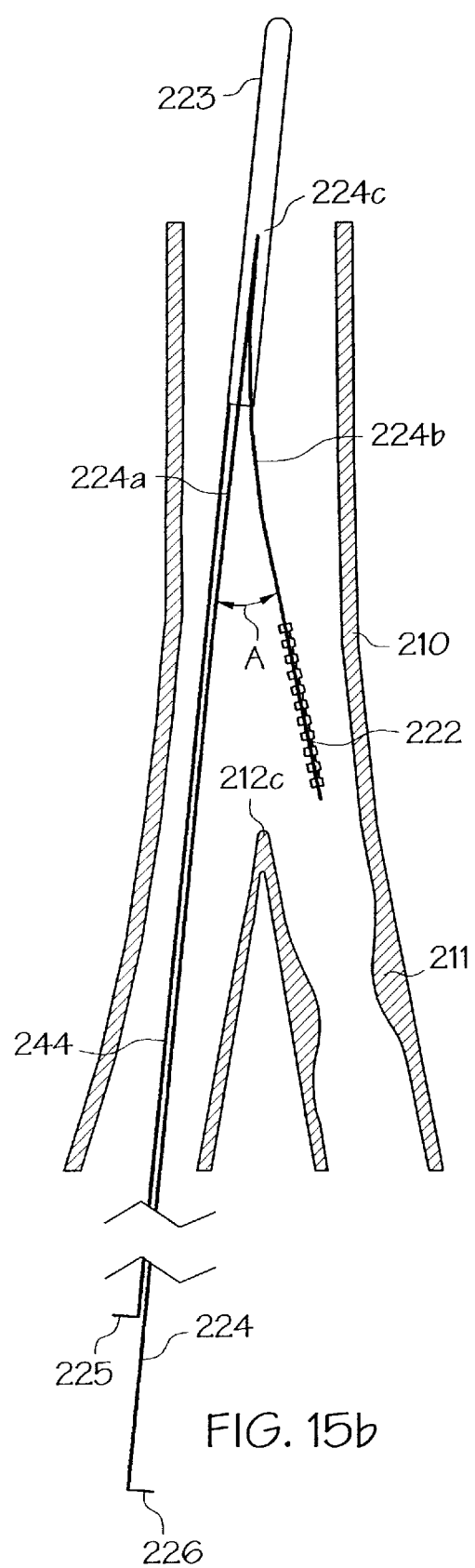
FIG. 15a
FIG. 15b

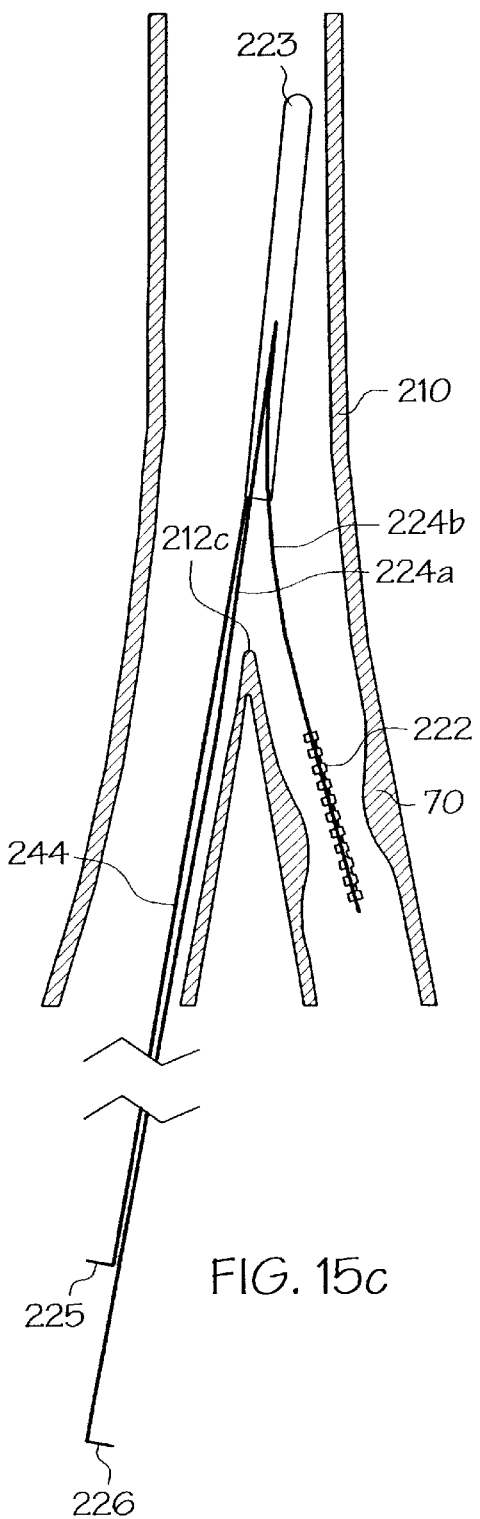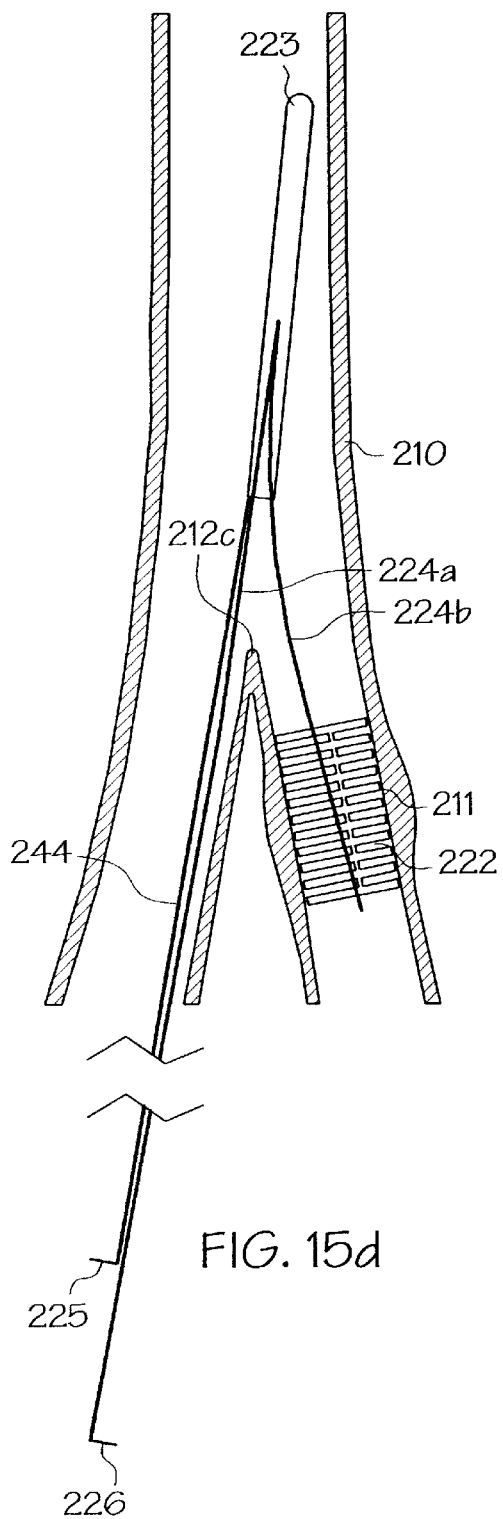

APPARATUS AND METHOD FOR PLACING BIFURCATED STENTS

BACKGROUND OF THE INVENTION

The present invention generally relates to a device and method for delivering an expandable endoluminal prosthetic device, such as a stent, and more particularly to a device and method for placing a bifurcated stent such that only a single incision into a patient need be made.

Expandable surgical devices, such as stents and angioplasty balloons, are used in a variety of places in the human body to support various anatomical lumens, such as blood vessels, respiratory ducts, gastrointestinal ducts and the like. Conventionally, these devices are deployed in regions of stenosis or constriction in the target body lumen to hold the lumen open, thus obtaining a patent lumen and preventing immediate or future occlusion or collapse of the lumen and the resultant obstruction of fluids flowing therethrough. Because stent and balloon implantation is a relatively noninvasive procedure, it has proven to be a favorable alternative to surgery in, for example, certain cases of vascular stenosis. Bifurcated devices, with their trunk and branching configuration, are particularly well-suited for use in branching body lumen systems, such as in the coronary vasculature (which include the right, left common, left anterior descending and circumflex arteries and their branches) and the peripheral vasculature (including branches of the carotid, aorta, femoral, popliteal, and related arteries). Placement of such a bifurcated device can be rather complicated, often involving approaching the bifurcated section of the artery through at least two side branches or through the trunk plus one side branch. This procedure can be not only time-consuming, but also lead to more incision sites in the patient's body, as well as necessitate more complicated maneuvers for the surgeon. Procedures for placement of a bifurcated stent are described in U.S. Pat. No. 5,720,735 to Dorros, entitled "Bifurcated Endovascular Catheter" and U.S. Pat. No. 4,994,071 to MacGregor, entitled "Bifurcating Stent Apparatus and Method". In these patents, which are representative of the state of the art, each of the branches has a dedicated guide wire to guide the placement of balloons, stents, stent grafts or grafts into a bifurcated anatomical lumen. This redundancy can lead to increases in the overall size, cost and complexity of delivery devices.

Accordingly, there exists a need for an apparatus used to place bifurcated stents and related surgical devices into a body lumen such that simpler surgical procedures are enabled, with a concomitant decrease in incision number or size and related invasive steps, thereby reducing patient trauma associated with complex medical procedures.

SUMMARY OF THE INVENTION

This need is met by the present invention, where the placement of a stent becomes simplified by the use of a single delivery catheter, using only a single incision in only one location. The present apparatus and method allow for placing non-bifurcating stents in a side branch of a bifurcating lumen, as well as for placement of all kinds of bifurcating stents anywhere in the body, with or without a graft. While it can be readily appreciated that the device described herein is applicable for use in numerous endoluminal devices, and in a variety of bifurcated body lumens, much of the subsequent discussion is limited to the example of a bifurcated stent for use in preventing an abdominal aortic aneurysm (hereinafter referred to as triple A), where such a device is commonly known as a triple A graft stent. Such a stent includes a near side branch section, far side branch section, and a trunk section joined to adjacent, or hinged ends of the two branch sections. Furthermore, it will be appreciated that the expansion of the triple A graft stent and related stents can be effected by plastic deformation due to balloon pressure, or triggering of elastically stored energy in the stent (such as with bistable stents or elastic or superelastic expansion).

According to an embodiment of the present invention, a catheter for inserting, deploying and removing a bifurcated surgical device is disclosed, where preferable surgical devices include bifurcated endoluminal stents, stent-grafts, grafts and balloon angioplasty mechanisms. The catheter, with an elongate hollow body, narrow proximal end and widened distal end is insertable into a single percutaneous incision site. The hollow body houses a central catheter wire that is used to deploy a stent mounted to the catheter. The distal end of the elongated body includes a flanged, exaggerated generally cylindrical portion configured to sheath the ends of the branch sections of the bifurcated stent, thus ensuring a small cross-sectional area for the entire as-inserted combination. The central catheter wire includes two leg portions connected at a common end to a trunk portion. The two leg portions of the central catheter wire are biased to a closed position, so that they are in a substantially side-by-side, parallel relationship, both effectively parallel with the trunk portion. This bias is important for establishing a small cross sectional area of the wire once the stent has been deployed. In stents that rely on balloons for expansion, this bias in the central catheter wire also helps to bring the deflated balloons together for improved ease of catheter removal. Prior to the deployment of the bifurcated surgical device, the bias is designed to be overcome by inherent spring forces in the branches of the bifurcated surgical device, which needs to expand to approximate the angle formed between the main and branching body lumens. This bias in the bifurcating surgical device is such that a substantially Y-shaped intersection is formed, which also induces the catheter to assume such a shape upon unsheathing of the bifurcating surgical device.

The coaxial arrangement between the components of the present system and the stent, as well as the relative axial movement between them permit both simple operation coupled with unobtrusive cross-sectional dimensions. Operability is further enhanced by the inclusion of position-indicating markers with steerable features. In addition to providing indicia of stent axial (or translational) position relative to the catheter, these markers provide readily-apparent indicia of the angular position of the device vis-à-vis the body lumen to enable accurate positioning of the stent. To enhance patient safety, the catheters of each of this and the following embodiments may optionally include a flexible housing that can follow the angular movements between the branches easily, while it smoothens the functioning of the device.

Alternately, the apparatus can be adapted to accept self-expanding stents, where the bifurcated balloon is replaced by multiple travelling sheaths that work in cooperation with tension and pushing elements within the catheter for removal of the sheaths from the stent surface. In this configuration, an additional wire, called a sheath deployment wire, is disposed adjacent the central catheter wire in the same hollow portion of the elongate body. The two wires work in conjunction with one another, as the sheath deployment wire is used to push the self-expanding stent and one or more of the stent-restraining travelling sheaths farther into the aorta such that the stent and sheaths are entirely beyond the body lumen bifurcation point. As previously discussed, the stent branches are of such spring bias that their tendency to splay is greater than the ability of the central catheter wire leg portions to stay together. This bifurcation allows one of the stent branches to be positioned in each of the iliac arteries upon partial pullback of the stent. Once the pullback has been accomplished, and the stent sheaths have been seated adjacent the body lumen bifurcation point, the central catheter wire, which now includes a series of mechanical stops along its trunk section, can be translated relative the stent such that it engages the travelling sheaths surrounding the far side branch and the trunk, moving them away from their corresponding stent sections, and permitting the stent to expand under its own elastic power. Once this is completed, the near side branch sheath can be removed by pulling back on the sheath deployment wire to allow expansion of the final stent section, at which time the catheter can be withdrawn therethrough, and out the incision.

According to another embodiment of the present invention, a catheter used for the deployment of a self-expanding surgical device is similar in structural attributes to the aforementioned alternate embodiment catheter, with an additional biasing sleeve to facilitate removal of the sheath and wire once the surgical device has been inserted. This results in a sandwich-like structure that surrounds the surgical device, and includes the central core catheter wire inside the inner surface of the self-expanding surgical device, a travelling sheath surrounding the outer surface of the surgical device, and a biasing sleeve disposed on the outer surface of the travelling sheath. Once the crush-resistant surgical device is pushed out from the travelling sheath and deployed in the body lumen, the contracting force of the biasing sleeve causes the travelling sheath to collapse into a smaller diameter, coming to rest substantially on or adjacent the central catheter wire. This reduced cross-sectional area makes it easier to remove the sheath and wire through the hollow inner core of the now-expanded surgical device without snagging or otherwise inadvertently engaging the surgical device.

According to another embodiment of the present invention, a catheter for delivering a non-branching stent can be placed into a side branch of a body lumen for situations where the catheter side branch makes an acute angle from the main lumen insertion direction, thereby overcoming the difficulty with which conventional catheters have had in reaching such a side branch. In this configuration, the main catheter, in contrast to the previous embodiment, does not have an elongate hollow body, instead comprising a core wire, sheath and sheath deploying wire. The core wire is further defined by a main body portion and a leg portion, where the main body portion extends from a user-graspable proximal end to a distal end, and the leg portion is hingedly attached to the main body portion's distal end and configured for transporting the stent. The inherent spring stiffness at the distal junction is such that the leg and main body portions are biased in an open position to form an acute angle roughly commensurate with the angle made between the main body and side branch lumens. The angled bias between the distal end of the core wire's main body portion and the joined leg portion can be overcome such that the remote end of the leg portion is pointing substantially toward the proximal end of the main body portion. In this compressed state, the cylindrical, substantially hollow sheath can be inserted over the distal junction, thus holding the main body and leg portions of the core wire in a substantially parallel configuration. The stent can be inserted over the remote end of the leg portion that protrudes beyond the open end of the sheath. As with the previous embodiments, the stent can be either self-expanding or balloon expandable. In the balloon-expandable variant, the core wire could be of hollow tubular structure to permit the passage of an expansion fluid or an additional wire therethrough. The use of a central catheter wire, surrounded by the thin-walled tube with high flexibility (made from, for example a superelastic Nitinol) is but one example. A catheter with such a tubular core wire has more longitudinal rigidity and gives a better support for accurate relative movements between the central catheter wire and the delivery sheath. Proximal actuation using such a configuration becomes much more controllable, thus facilitating the user's task.

According to another embodiment of the present invention, a stent delivery catheter comprising an elongate body, central catheter wire and a stent release wire is disclosed. The elongate body includes a proximal end, a distal end sufficiently enlarged relative to the proximal end so as to sheath an engaging end portion of a stent, and a hollow core extending between the proximal and distal ends. The central catheter wire fits through the hollow core, and is positionable relative to the hollow core. The central catheter core wire is made up of a main body portion with a user-graspable proximal end and a distal end, and a leg portion comprising a distal end joined to the distal end of the main body section to form a hinged relationship therebetween and a remote end engageable with the stent. The stent release wire is disposed within and positionable relative to the hollow core in much the same way as the central catheter wire. The stent release wire is defined by a main body portion with a user-graspable proximal end and a distal end configured to engage the stent and the remote end of the leg portion. As with the previous embodiment, the central catheter wire may be of hollow tubular construction to permit the placement of another wire or fluid supply line therein.

According to yet another embodiment of the present invention, a method for inserting a bifurcating surgical device, such as a stent, is disclosed. The method includes bringing the stent into place by advancing the whole stent in a delivery catheter with restraining sheath through a single incision location. By way of example, this single incision could be through a main side branch artery in a patient's leg. The distal end of the delivery catheter holding the stent is inserted until it arrives adjacent the aneurysm area, with the lower ends of the stent branch sections beyond the body lumen bifurcating point, where the aorta divides itself into the two common iliac arteries. Upon insertion beyond this bifurcating point, a restraining sheath is pulled back, thereby exposing the unconnected ends of the two branch sections. The stent is still in its unexpanded state, but the elasticity of the two branch sections of the stent tends to create an angle between the two hingedly connected branch sections. In the present context, two or more members are considered to be hingedly connected when they are joined at a common end, regardless of how they are attached, such that only relative rotational movement (with no translational component) is permitted at such connected end, while the opposing unconnected ends are free to move relative to one another, constrained only by resistive forces operating at the connected end. A resiliently biased connection could include hingedly connected members that exhibit elastically deformable properties such that upon removal of a constraining force, the members would revert back to a predetermined unconstrained spacing relative to one another. By proper engineering choice of the elastic force, the amount of spread between the unconnected ends of the branch sections is such that they can gently be pulled back into their respective arteries, while the trunk section of the stent is also pulled back into the final artery section, where the aneurysm is located.

Once the stent is properly positioned relative to the iliac arteries and the lower aorta, the whole stent can be expanded into the final shape, by, for example, either self-expansion features integral to the stent, or by a conventional expander (typically a balloon) located within the delivery catheter. In the former case, the stent may be made of a shape-memory material. In the latter case, the balloon can either be made from one single piece, with the same overall shape as the bifurcated stent, or from several sections that can be inflated at different times. With such a bifurcated balloon, the whole stent can be expanded without repositioning of the balloon and, if needed, can be done very fast, thus reducing critical operation time. After deflating, the balloon can then be moved in the catheter insertion (distal) direction until the free end of the far side leg portion is moved completely beyond the body lumen bifurcation point and into the trunk section of the aorta. The two branch sections of the bifurcating balloon have been made elastic as well, but in a different way than the branch sections of the stent, such that they are biased to a substantially parallel orientation in line with the trunk of the balloon. One way this biasing can be achieved is by using two elastic spring wires, strips or tubes made from straight superelastic Nitinol, or related shape-memory material, disposed either in or outside the center of the balloon branch sections, coming together in or near the center of the balloon trunk. Thus, in addition to the two opposing bias forces previously discussed, where the branch sections of the stent have to move apart for placement and the leg portions of the central catheter wire have to move together for easier removal, the presence of the balloon bias further reinforces the closing tendency of the catheter so promote the small cross-sectional area necessary to ensure ease and safety of catheter removal. Thus, once the stent has been deployed, and the catheter with the deflated balloon has been pushed into the trunk section of the aorta, the balloon branch sections snap back to their parallel position and the whole catheter with the deflated balloon can be withdrawn from the body through the incision site. For additional safety and reduction of the pull-out force required, the exaggerated distal end of the catheter's elongate body can re-sheath the two leg portions of the central catheter wire that engage the branch sections of the balloon. An elastic sleeve can optionally be used to surround the balloon, thereby minimizing the balloon geometry after deflation by applying a biasing load on the balloon. This acts to decrease deflation time, as well as control the timing of inflation over the balloon length or influence the final dimensions during and after inflation.

According to still another embodiment of the present invention, a method of inserting a side branching stent is disclosed. After the stent is brought beyond the body lumen bifurcation point, the restraining sheath that held the wire sections parallel is removed by pushing farther into the distal direction. The natural bias of the distal junction then forces the predisposed angle between the core wire's main body and leg portions. Once the angle inherent in the spring bias is established, the catheter is pulled back in proximal direction, causing the catheter to enter the side branch of the lumen that has to be treated. After deployment of the stent, the catheter is pushed into the initial direction of insertion until the remote end of the leg portion is again beyond the body lumen bifurcation point. The catheter sections are then brought into their parallel position by reinsertion into the sheath, and then the whole device is pulled out through the initial insertion location.

The catheter used to insert the side-branching stent can include an elongate hollow body, a core wire and a release wire. In this configuration, the central catheter core wire may be of hollow tubular construction (as hereinbefore discussed in conjunction with previous embodiments) to permit the placement of at least the release wire or a fluid supply line (if needed) therein. Such an arrangement promotes both relative motion between the components, as well as small footprint of the stent deployment mechanism.

Other objects and advantages of the invention will become more apparent after reference to the following description, the accompanying drawings and the appended claims.

BRIEF DESCRIPTION OF THE DRAWINGS

FIG. 4 shows the inflation of the balloon and its expansion effect on the stent;

FIG. 5 shows balloon in a deflated condition once the stent has been secured to the aorta and iliac arteries;

FIG. 6 shows the tendency of the angle between the central catheter wire leg portions to close when the catheter is moved beyond the body lumen bifurcation point;

FIG. 7 shows the retraction of the central catheter wire and the balloon into the sheath of the catheter just prior to removal of the entire assembly from the body lumen;

FIG. 15a shows a stent delivery catheter according to another embodiment of the present invention for use in the insertion of a stent into a body lumen side branch;

FIG. 15b shows the placement of the stent beyond the body lumen bifurcation point, as well as the tendency of the core and leg portion wires to bifurcate upon removal of the restraining sheath;

FIG. 15c shows the pulling back of the stent into seating relationship with the body lumen bifurcation point;

FIG. 15d shows the stent in its expanded condition and placed adjacent an arterial lesion;

DETAILED DESCRIPTION OF THE INVENTION

Figure 1:
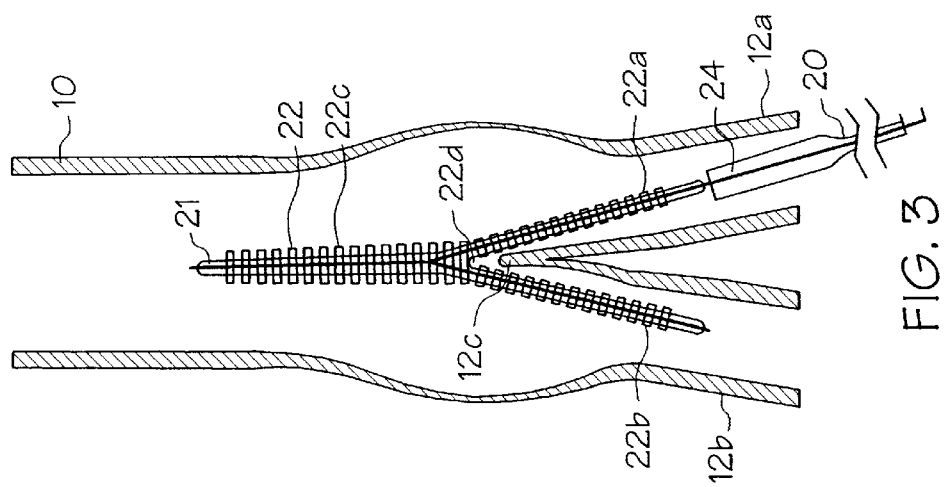
FIG. 1 shows the first step of the insertion of a stent delivery catheter with balloon, stent and a delivery sheath upon insertion into an aorta, according to an aspect of the present invention.

FIG. 1 shows an aorta 10 with an aneurysm 11 and two common iliac arteries 12a and 12b. According to a first aspect of the present invention, a delivery catheter 20 with proximal and distal ends 20a and 20b, respectively, is shown partially inserted into aorta 10, carrying with it an uninflated balloon 21 and a bifurcated stent 22 with branch sections 22a and 22b and trunk section 22c. The balloon 21 is made up of branches 21a, 21b and trunk 21c. Distal end 20b of delivery catheter 20 is widened to define a retractable delivery sheath 23 that holds stent branch sections 22a and 22b in parallel. Although stent 22 is configured representatively as an axial series of expandable rings, connected by a longitudinal backbone elements 22e and 22f (shown in more detail in FIGS. 4-7), its geometry can be any conventional expandable kind capable of producing desirable structural properties, and is therefore not described in further detail. The catheter 20 has a hollow core 20c that encases a central catheter wire 24, which is used to translate the balloon 21 and stent 22 relative to the delivery sheath 23 of catheter 20. The catheter 20, balloon 21 and stent 22 are inserted into a patient at some remote location, such as in a leg portion (not shown). The catheter 20 is strong and stable enough to enable it to be moved through the body lumen without buckling. It is further desirable that the catheter 20 is made steerable over the range of insertion such that, upon application of a torsional force by a user's hand, it can be easily rotated and positioned in the patient's body. In the balloon-expandable genre of stents, hollow core 20a further requires a fluid supply line (not shown) to transport expansion fluid from an external source and into the balloon to provide sufficient inflation force.

The proximal end of central catheter wire 24 includes a first marker 25 to enable a user to check the longitudinal position of the central catheter wire 24 in relation to a second marker 26 located on catheter 20. Comparison of the distance between markers 25 and 26, shown as X, allows the user to determine the position of the two branch sections 22a and 22b relative to the end of delivery sheath 23. Thus, when the markers 26 and 25 are brought together, their close juxtaposition indicates that the stent 22 and balloon 21 are outside the sheath 23. The markers 25 and 26 additionally function to provide the user with readily apparent visual information about the rotational position of the two branch sections 22a and 22b in relation to the position of the two common iliac arteries 12a and 12b. This ensures that, prior to stent expansion, branch 22b is in its proper rotational position with respect to iliac artery 12b, as it points to the right (as depicted in the figure) when branch section 22b is aligned with iliac artery 12b.

Figure 2:
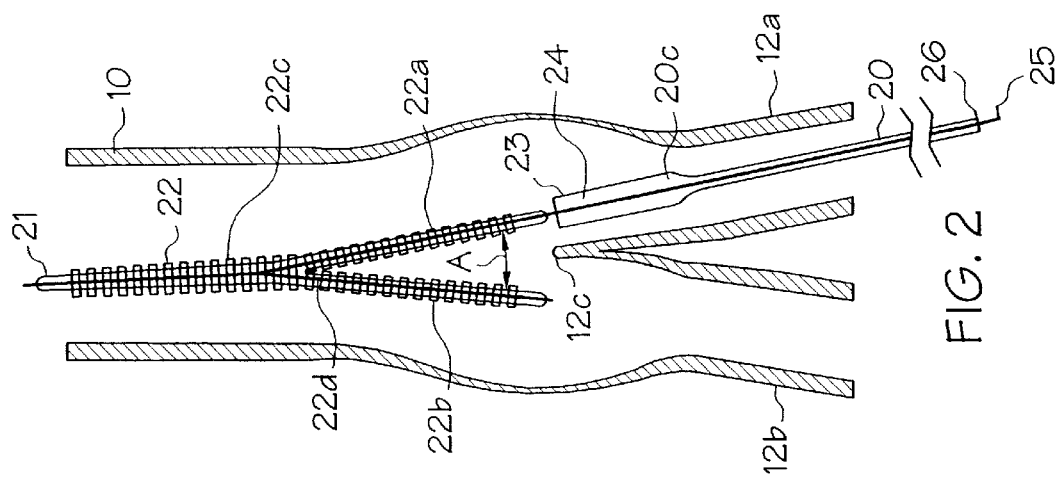
FIG. 2 shows the tendency of the stent, balloon and central catheter wire of FIG. 1 to splay when unsheathed.

FIG. 2 shows that once the stent 22 has been inserted beyond body lumen bifurcation point 12c, the delivery sheath 23 may be retracted so that stent branch sections 22a and 22b are released, enabling them to open up under their own elastic separating force to create an angle A between them, where they split from the trunk section 22c at the stent bifurcating point 22d. In addition to the aforementioned configurational choices, the elastic properties of the stent can be controlled by proper material choices, where polymers, metals, memory materials with superelastic or temperature dependant behaviour, organic materials, ceramics and combinations thereof can be especially useful. Similarly, such approaches can be used for some of the other elements used to enable catheter functioning, such as the central catheter wire 24 that, through integral bifurcating features, interacts with the opening force of the stent branch sections 22a, 22b. In one example, a suitable material would be Nitinol, a nickel-titanium alloy with shape-memory properties that allow high elastic strain and the stable forces over a high strain range. The branch sections 22a, 22b of the stent 22 can be programmed to take a preferable parallel position by means of heat treatment of the Nitinol. The tendency of the stent branch sections 22a, 22b to open up their relative angle can also be influenced by some additional elastic wires, strips, tubes or sheaths, made from Nitinol or any other suitable material. Designed-in elastic properties of stent 22 can alternatively come from the aforementioned backbone-like elements 22e, 22f that connect a series of ring segments of the stent in an axial direction, or could be stored in some other body, such as a segment of graft material (not shown) brought in place together with the stent 22.

Figure 3:
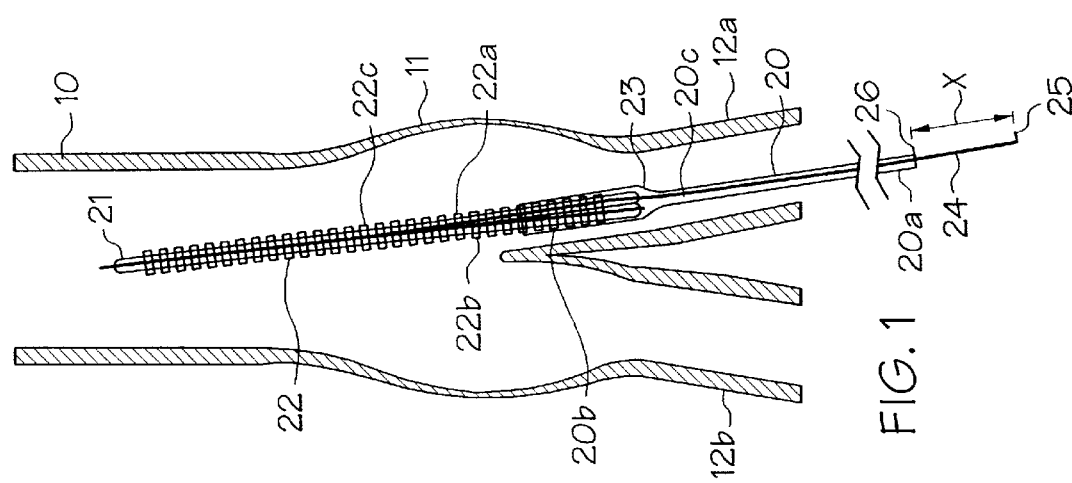
FIG. 3 shows the placement of the stent, balloon and central catheter wire of FIG. 2 into cooperative engagement with the body lumen bifurcation point.

Referring now to FIG. 3, the catheter 20 with the uninflated balloon 21 and unexpanded stent 22 are brought into position by pulling back on the catheter 20 until body lumen bifurcation point 12c of aorta 10 and stent bifurcation point 22d are brought into their desirable relative position. The angular bias provided by the branch sections 22a and 22b ensures that when catheter 20 is pulled back, stent bifurcation point 22d will seat itself adjacent body lumen bifurcation point 12c. When this occurs, stent 22 is ready for expansion in order to reach the walls of arteries 12a, 12b.

FIG. 4 shows stent 22 placed in its final destination in an expanded state, along with inflated balloon 21. Together, trunk 24c and leg portions 24a, 24b define a central spring element that has the tendency to close the angle A between the stent branch sections 22a, 22b that gets formed when they bifurcate. To augment the angle-closing bias of the central catheter wire 24, which is made up of multiple sections, including first leg portion 24a, second leg portion 24b and trunk 24c, all joined together at bifurcation point 24d, an additional sleeve or ring can be pulled over bifurcation point 24d of the central catheter wire 24, thereby keeping the leg portions 24a, 24b together. Despite the tendency of the central catheter wire leg portions 24a, 24b to go to their preferable parallel position, they are kept open because they touch the inner wall of the stent 22 near bifurcating point 22d, as shown in the figure. In addition, catheter central wire trunk 24c and leg portions 24a and 24b serve as a framework for the surrounding balloon branches 21a and 21b and balloon trunk 21c. The active biasing pressure of the sleeve can determine the threshold pressure for inflation, and so the sequence of expansion of the stent 22 can be controlled. The tendency of the stent 22 branch sections 22a and 22b to create angle A in FIG. 2 is strong enough to overcome the biasing force of the central catheter wire leg portions 24a and 24b, which would otherwise tend to close the angle A. An example of an elastic element in the stent 22 that has the tendency to open up the angle is shown as the backbone elements 22e and 22f, integrated in the surface of the stent 22. One or more fluid supply lines (not shown) provide expansion fluid to inflate balloon 21 through, for example, side holes to allow the expansion fluid to enter into the balloon sections 21a, 21b, 21c for inflation. If desired, the pattern and sequence of inflation of the different balloon sections can be controlled in time by having multiple fluid supply lines disposed in catheter hollow core 20c 24 that are connected to multiple lumens. An alternative method, that only requires a single fluid supply line, is the use of a surrounding biasing sleeve that hinders the inflation of balloon sections in a different way along the length of the balloon.

FIG. 5 shows the catheter 20 in the same position as in FIG. 4, with the balloon 21 now deflated. The stent 22 sections 22a through 22d form a tight fit with the surrounding aorta 10 and arteries 12a, 12b. One or more longitudinally disposed stent backbones 22e, 22f provide axial structure and stability. Stent 22 can also be used with a graft (not shown) that surrounds, or is surrounded wholly or partly by it. Balloon sections 21a, 21b and 21c return to their smaller, as-inserted diameter and closely surround their respective catheter central wire leg portions and trunk 24a, 24b and 24c. This can be achieved by making the balloon 21 from either an elastic material, or by combining an elastic biasing material with a less compliant underlying balloon section (not shown).

FIG. 6 shows how the catheter 20 has been moved farther into the iliac artery 12a such that the end of leg portion 24b and balloon branch 21b are clear of body lumen bifurcation point 12c. This allows the leg portions 24a, 24b of the catheter central wire 24 spring back to their preferable parallel position, bringing the deflated balloon branches 21a, 21b with them. The stent 22, now firmly lodged in aorta 10 and iliac arteries 12a, 12b, is left in place while delivery sheath 23 can be further pushed inward such that its distal end is beyond body lumen bifurcation point 12c to engage the now substantially parallel ends of balloon branches 21a, 21b.

FIG. 7 shows the catheter 20 with the delivery sheath 23 reinserted over the ends of the balloon branches 21a and 21b as evidenced by distance X between markers 25 and 26, to enable removal from the patient's body. This ensures the narrow cross sectional area and resultant lower friction to minimize the risk of injury that could otherwise be caused by the free end of the central catheter wire leg portion 24b piercing the artery wall upon withdrawal. As shown in this figure (as well as FIGS. 5 and 6), the size of the deflated balloon 21 is smaller than the inner diameter of the expanded stent 22 to enable free movement of the balloon 21, the central catheter wire 24 and its leg portions 24a, 24b upon removal. In this regard, the use of a biasing sleeve (not shown) around the balloon 21 can be very helpful in not only maintaining the circular cross sectional area of balloon 21 upon deflating, but also by minimizing its size. Further, the active biasing forces of the elastic sleeve can speed the deflation process.

Figure 8:
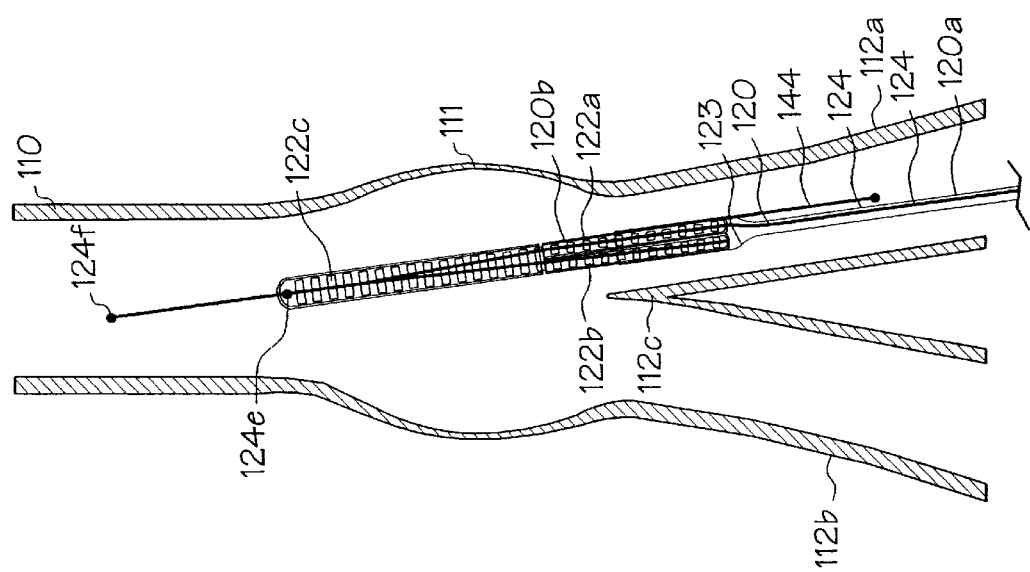
FIG. 8 shows a variation of the stent delivery catheter, where the balloon-expandable stent has been replaced by a self-expanding stent.

Referring now to FIG. 8, another aspect of the present invention is shown, where a delivery catheter 120 surrounding a self-expanding stent 122 with branch sections 122a, 122b and trunk section 122c, is placed adjacent the aorta 110 with an aneurysm 111 and the two common iliac arteries 112a and 112b. The delivery catheter 120 has a narrow proximal end 120a and a wider distal end 120b that holds the stent branch sections 122a and 122b parallel. The inside of catheter 120 is hollow such that it houses central catheter wire 124 in a manner similar to the embodiment shown in FIGS. 1–7, where central catheter wire 124 can be pushed and pulled by the user. Also, as with the previous embodiment, a delivery sheath 123 is defined at the wider distal end 120b of catheter 120. A second, sheath deploying wire 144 (to be discussed in more detail later) is disposed adjacent central catheter wire 124.

Figure 10:
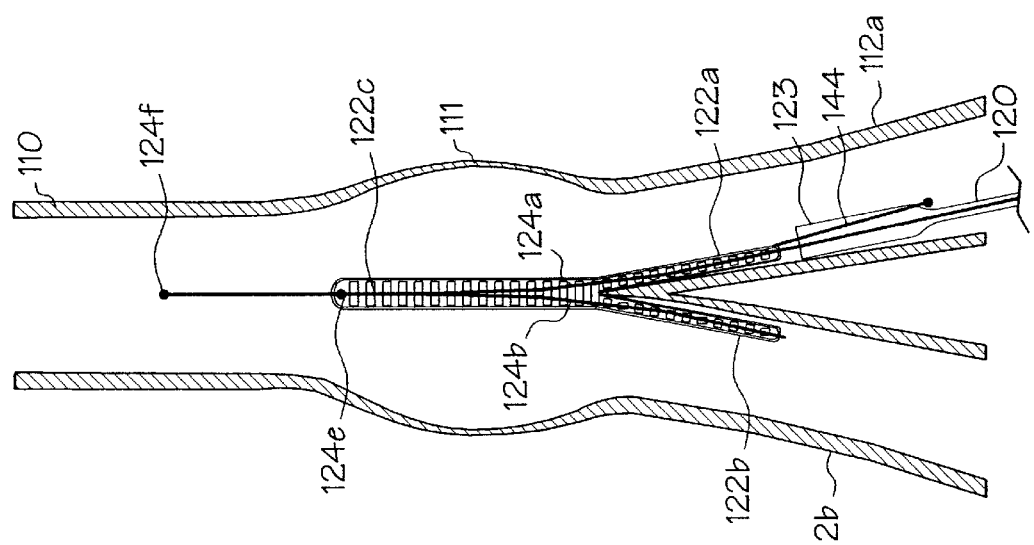
FIG. 10 shows the use of the central catheter wire to pull back the stent and sheaths into a seating arrangement with the body lumen bifurcation point similar to that of FIG. 3.
Figure 9:
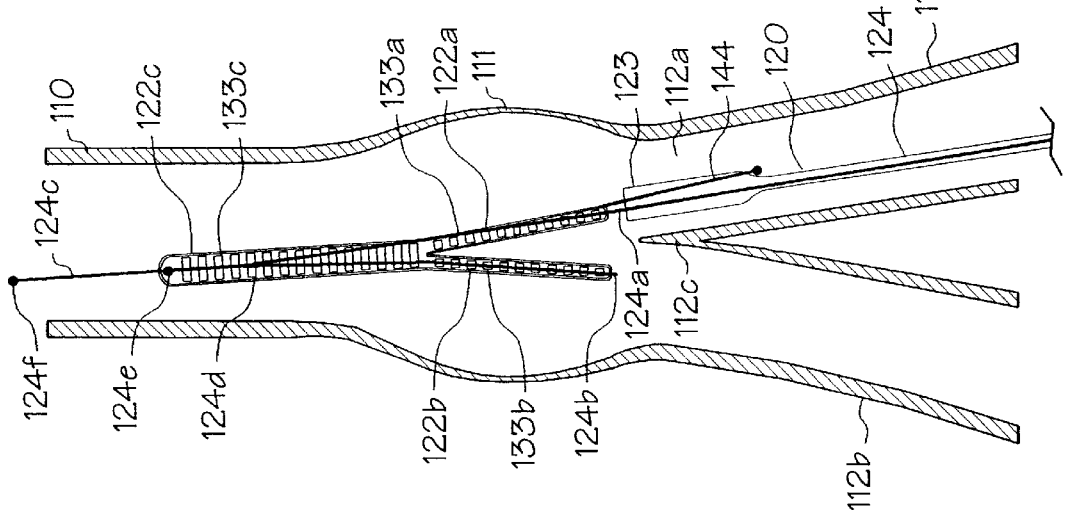
FIG. 9 shows the use of a stent sheath deployment wire to push the stent and travelling sheaths beyond the body lumen bifurcation point, enabling opening bias similar to that of FIG. 2.

Referring now to FIGS. 9 and 10, once the various stent sections 122a, 122b and 122c are beyond the body lumen bifurcation point 112c, the delivery catheter 120 is pulled back to release the stent branch sections 122a and 122b and enable them to open up. Similar to the first embodiment, central catheter wire 124 is capable of bifurcation, having two branch sections 124a and 124b that join together with trunk section 124c at bifurcation point 124d. Additionally, travelling sheaths 133a, 133b and 133c are disposed around each of the stent sections 122a, 122b and 122c respectively, such that the stent sections are encased until such time as stent placement and expansion is desired. First mechanical stop 124e is configured to engage the inner distal end of travelling sheath 133c such that, upon appropriate translational force applied by central catheter wire 124, travelling sheath 133c can be separated from stent trunk section 122c. FIG. 10 shows with particularity how the catheter 120 with the unexpanded stent branch sections 122a, 122b and unexpanded stent trunk 122c, all with travelling sheaths 133a, 133b and 133c, are brought into position by pulling back on the catheter 120 in a manner similar to that shown in FIG. 3.

Figure 11:
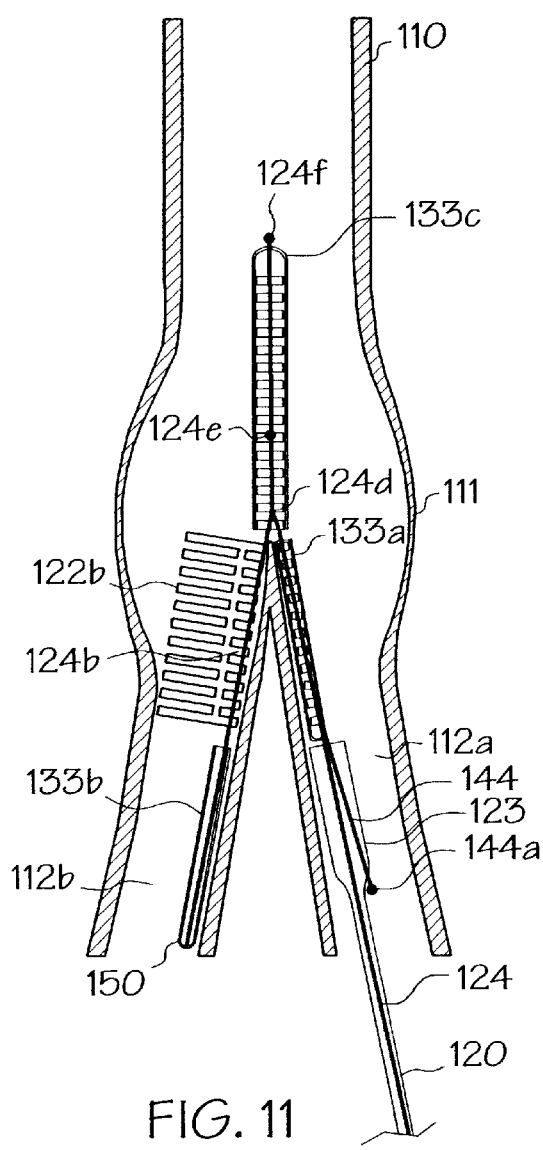
FIG. 11 shows the use of mechanical stops connected to the central catheter wire pulled in a proximal direction to effect removal of the travelling sheath from one of the stent branches.

Referring now to FIG. 11, the distal end of central catheter trunk section 124b is connected to the end of travelling sheath 133b such that upon the application of a downward translational force imparted by central catheter wire 124 through trunk section 124b, stent sheath 133b moves past the end of stent branch section 122b, forcing its release, as stent branch section 122b assumes its expanded position upon removal of the restraints imposed by travelling sheath 133b. The engagement point that coincides with the joined distal end of central catheter trunk section 124b and the end of travelling sheath 133b enables a smoother release (with less likelihood of stent sheath buckling) than when the sheath had to be pushed. The bifurcation point 124d of the central catheter wire 124 was originally above the bifurcation point of the stent (as can be seen in FIG. 9); whereas in the present figure it has moved downward while travelling sheath 133b was pushed down, with the mechanical stop 124f of the main wire has slid downward to engage travelling sheath 133c. The mechanical stop 124e has slid downward together with the central catheter wire 124. After having pushed out the stent branch section 122b, the travelling sheath 133b is empty and cocoon-like. One way to minimize the size is through the introduction of an elastic biasing sleeve 150 that can be placed around the outer surface of travelling sheath 133b. The biasing sleeve 150 can be configured from a rather rigid material with a well-defined geometry and maximum inner diameter that fits well around the stent branch section 122b. For the biasing sleeve around this delivery stent 123, the function is to compress the inner sleeve with a radial compression force to make it as small as possible. By crushing the travelling sheath 133b, a smaller diameter results, thus reducing the chances that the now empty sheath 133b will catch on the stent branch section 122b upon removal of the former from the latter. Accordingly, the biasing sleeve 150 can be any thin-walled conventional material, so long as it provides sufficient force on the travelling sleeve 133b to crush the sheath diameter upon release of stent branch section 122b. The interaction between the compressed stent 122b, the travelling sheath 133b and the biasing sleeve 150 has to be optimized to achieve the best combination of ease of stent delivery plus small cross-sectional profile for the catheter 120 upon removal. This requires that not only must the sheath be capable of being crushed once the stent branch section 122b is deployed, but also ensuring that the travelling sheath 133b is rigid enough to avoid premature deployment of the stent 122b disposed therein.

Figure 12:
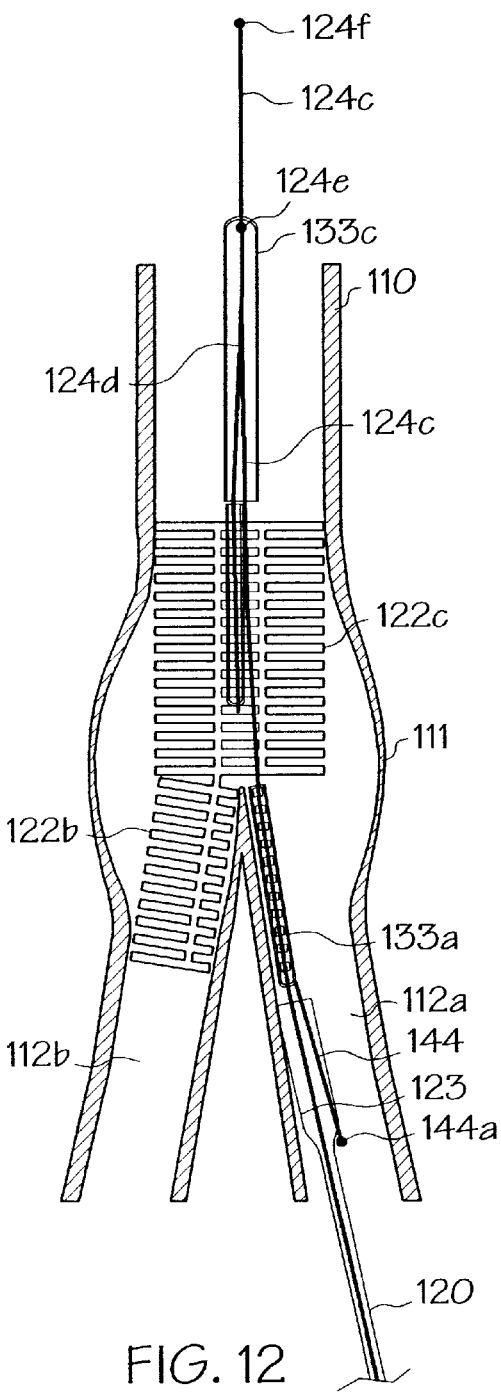
FIG. 12 shows the use of the mechanical stops of FIG. 11 pushed in a distal direction to effect removal of the travelling sheath from the stent trunk.

FIG. 12 shows how the central catheter wire 124 trunk section 124c, working in conjunction with mechanical stop 124e has pushed the travelling-sheath 133c upward to release the trunk section 122c of the stent. The function of mechanical stop 124e is that while the central catheter wire 124c can slide freely through the hole in the distal end of travelling-sheath 133c, once it reaches the position of mechanical stop 124e, the stent-sheath 133c is carried along with trunk section 124c as it is pushed up. It further shows how the catheter has been moved higher into aorta 110, where the leg portions 124a, 124b spring back to their preferable parallel position. Further, a sheath deploying wire 144 with mechanical stop 144a is attached to the lower end of the travelling sheath 133a to pull it downward. This wire 144 can be disposed substantially parallel to central catheter wire 124 and leave the patient's body at the proximal end of the catheter 120, although this is not necessary. A hole in the flange portion of delivery sheath 123 permits the sheath deploying wire 144 to run freely through the delivery sheath 123 of catheter 120 until mechanical stop 144a engages the wall of the flanged portion. From that position, the surgeon can pull catheter 120 down, thus removing travelling sheath 133a from stent branch section 122a.

Figure 13:
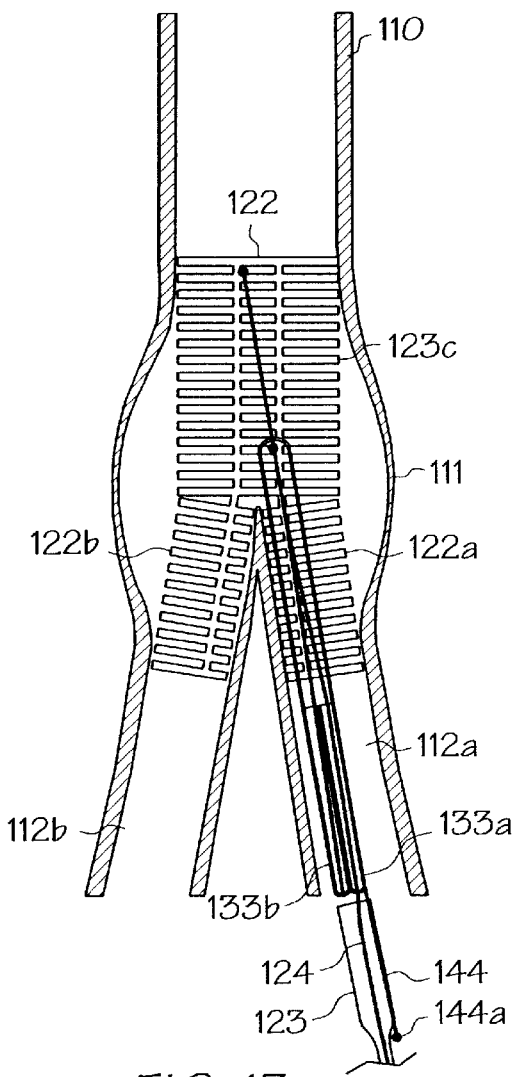
FIG. 13 shows the use of the stent sheath deployment wire to pull the travelling sheath off the remaining stent branch, in addition to the use of the central catheter wire to bring the travelling sheaths into operative contact with one another.

Referring now to FIG. 13, the central catheter wire 124 has been pulled down to bring the travelling-sheaths 133a, 133b down through the expanded stent sections 122c, 122a such that the travelling-sheaths 133a, 133b are lying beside each other in a substantially parallel arrangement. The cross sectional area of the adjacent travelling-sheaths 133a, 133b is small enough that they can be inserted into delivery sheath 123. The engagement of mechanical stop 124f with travelling sheath 133c has the effect of pulling down travelling sheath 133c into contact with the remaining travelling sheaths 133a, 133b similar to that of the as-inserted position depicted in FIG. 8.

Figure 14:
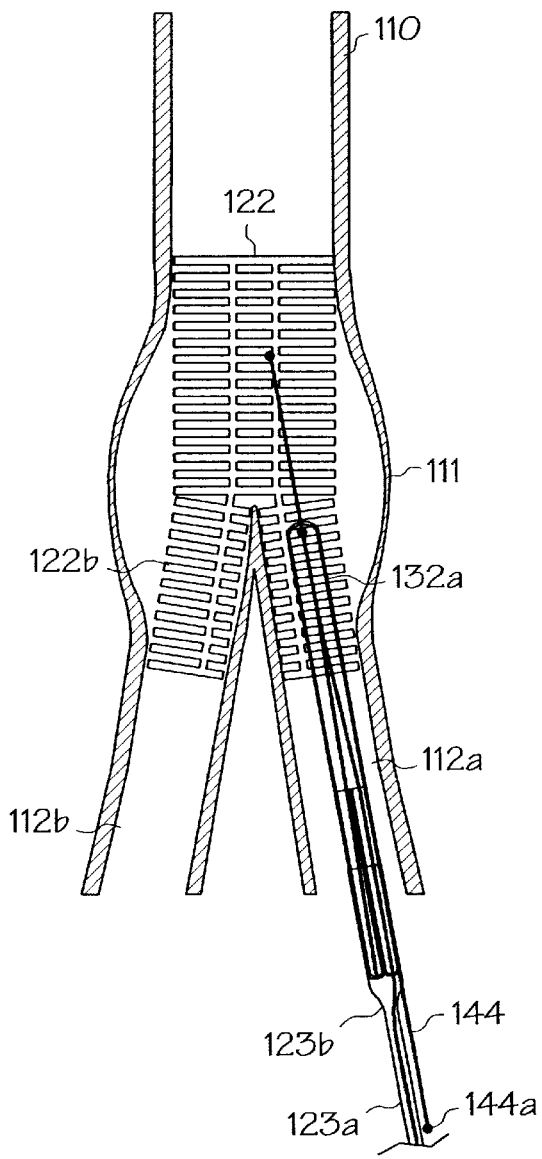
FIG. 14 shows the use of the reintroduction of the travelling sheaths into the distal end of the catheter prior to withdrawing the catheter from the incision site.

FIG. 14 shows the catheter 120 with the delivery sheath 123 shifted upward over the ends of the catheter branch sections 122a, 122b to enable removal from the patient's body. Sheath deploying wire 144 with mechanical stop 144a now extends from delivery sheath 123, but lies substantially parallel to the narrow portion of catheter 120 in a tight formation in order to avoid difficulty in removing the catheter from the patient's body. As with the previous embodiment, it is helpful if the cross-sectional area of the various components are minimized prior to catheter 120 removal from the patient's body.

Figure 15E:
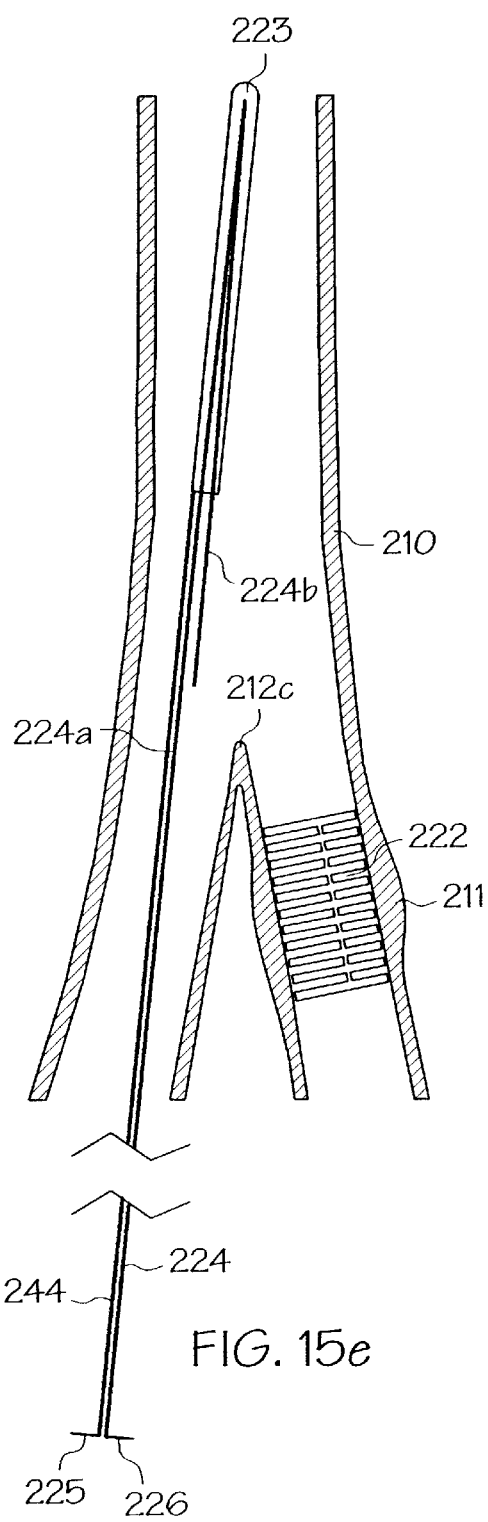
FIG. 15e shows the resheathing and removal of the leg portion wire by pushing the catheter in a distal direction beyond the body lumen bifurcation point.
Figure 15F:
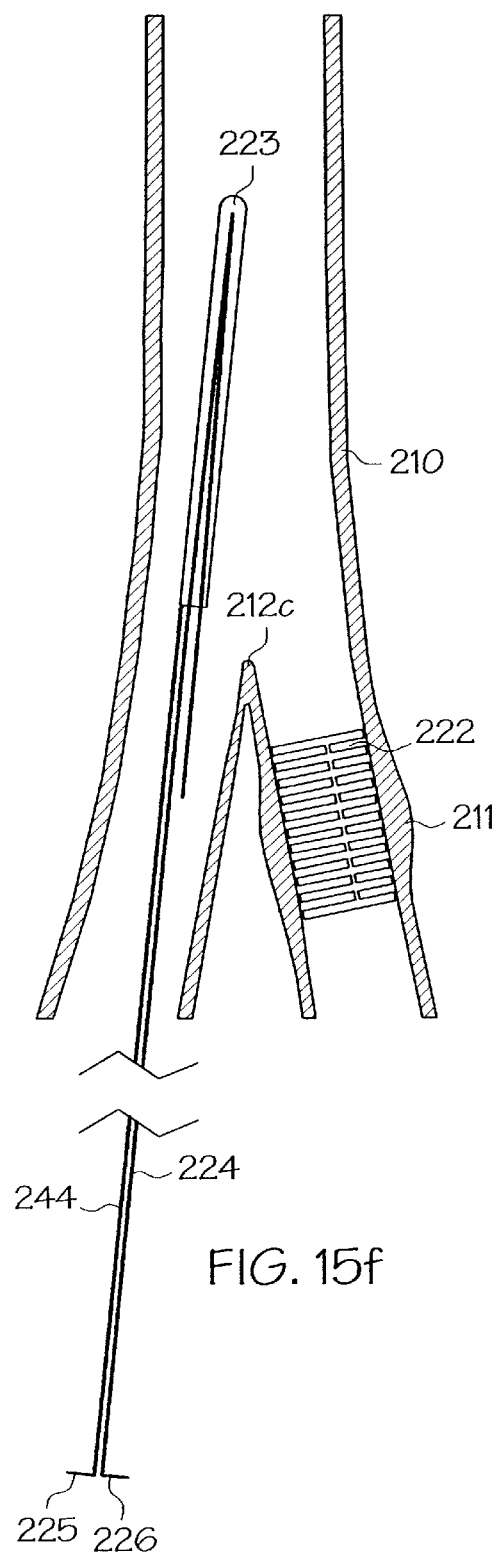
FIG. 15f shows the removal of the catheter from the aorta prior to exiting the incision site.

Referring now to FIGS. 15a through 15f, another embodiment of the present invention for use in main-to-side branch body lumens is shown. Here, a single stent 222 is placed into a side branch 210b of a body lumen 210, which is difficult to reach with conventional catheters. Side branches 210b that engage the main lumen 210 in an acute angle are amenable to the insertion of a catheter 220 according to the present embodiment of the invention for the purpose of putting an angioplasty balloon (not shown) or stent 222 into place. In FIG. 15a, such a bifurcating lumen 210 is shown with a lesion 211 in the side branch 210b of body lumen 210. A long core wire 224 includes a main body portion 224a and a leg portion 224b that are hingedly connected at a distal junction 224c. The leg portion 224b also contains the angioplasty balloon (not shown) or stent 222. Restraining sheath 223 can hold the core wire's main body and leg portions 224a, 224b parallel, and can be moved relative to the stent 222 and the core wire 224 by sheath deploying wire 244. As with the previous embodiment, both the core wire 224 and the sheath deploying wire 244 include markers 225 and 226 respectively, to assist the user in determining proper angular and translational positioning of the stent within the body lumen 210. As shown in FIG. 15b, after bringing the substantially parallel main body and leg portions 224a, 224b beyond the body lumen bifurcation point 212c, the sheath 223 that held the sections parallel is removed by sliding it farther through body lumen 210 by pushing on sheath deploying wire 244. Upon removal of sheath 223 from a significant portion of leg portion 224b of core wire 224, the spring bias forces the now unrestrained remote end to create an angle A with the main body portion 224a. As shown in FIG. 15c, the wire 224 and sheath 223 are pulled back toward the body lumen bifurcation point 212c, while the stent 222 enters the lumen side branch 210b with the lesion 211. As shown in FIG. 15d, the stent 222 has been expanded by one of the methods as have been described hereinbefore. This can include balloon expansion methods, where the wire takes on a tubular configuration such that it is capable of transporting expansion fluid to the distal end of leg portion 224b through its hollow center (not shown). In such a hollow configuration, the core wire 224 could also be used to house one or more, such as sheath deploying wire 244. This can be further advantageous in situations that employ a wedge ring (discussed below). FIG. 15e shows the leg portion and main body portion of core wire 224 being pushed in a distal direction until the remote end of leg portion 224b is beyond the body lumen bifurcation point 212c. FIG. 15f shows the leg portion being brought into a substantially parallel position with main body portion of the wire 224, reinserted into and secured by sheath 223. After that, the whole device can be pulled out in the proximal direction toward the incision (not shown) without risk.

Alternative ways to create an angle between the core wire 224 and side branch wire 224b are also possible. One example is the proximal actuation of a sliding wedge ring 260 (shown for clarity only in FIG. 15a) that is forced between the two parallel wires to push them apart. This embodiment works in conjunction with the embodiment of FIGS. 15a–15f, where the wedge ring 260 may be a separate structure, or may occupy the proximal end of sheath 223 such that it can decouple from the remainder of the sheath. The sheath deploying wire 244, or another, separate wire (not shown) could be connected to the wedge ring 260 to facilitate is axial movement relative to either the sheath 223, the core wire 224, or both. Sliding back of the wedge ring 260 allows the closure of the angle A between main body and leg portions 224a, 224b. The wedge ring 260 can also be used in reverse, where by proximal actuation of the ring, the angle A can be opened by releasing the wire portions so that the bias of the wire portions to splay promotes separation of the leg portion free end from the main body portion.

Figure 16A:
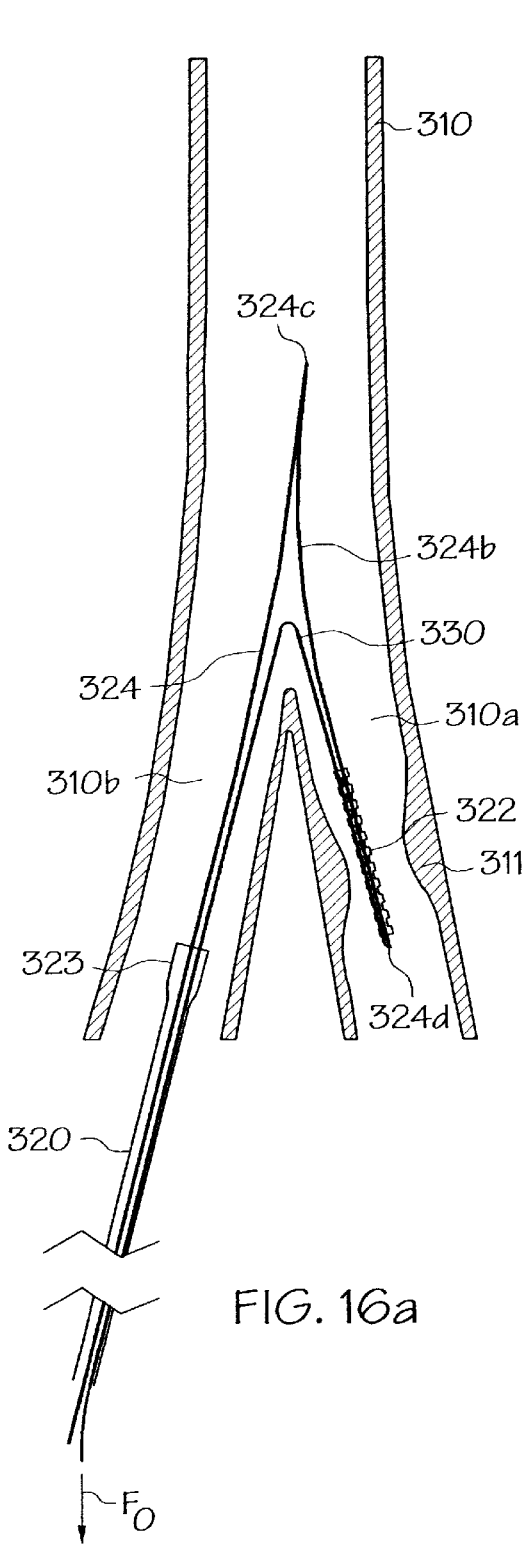
FIG. 16a shows a stent delivery according to another embodiment of the present invention that includes a pull wire at the distal end of the side branch.
Figure 16B:
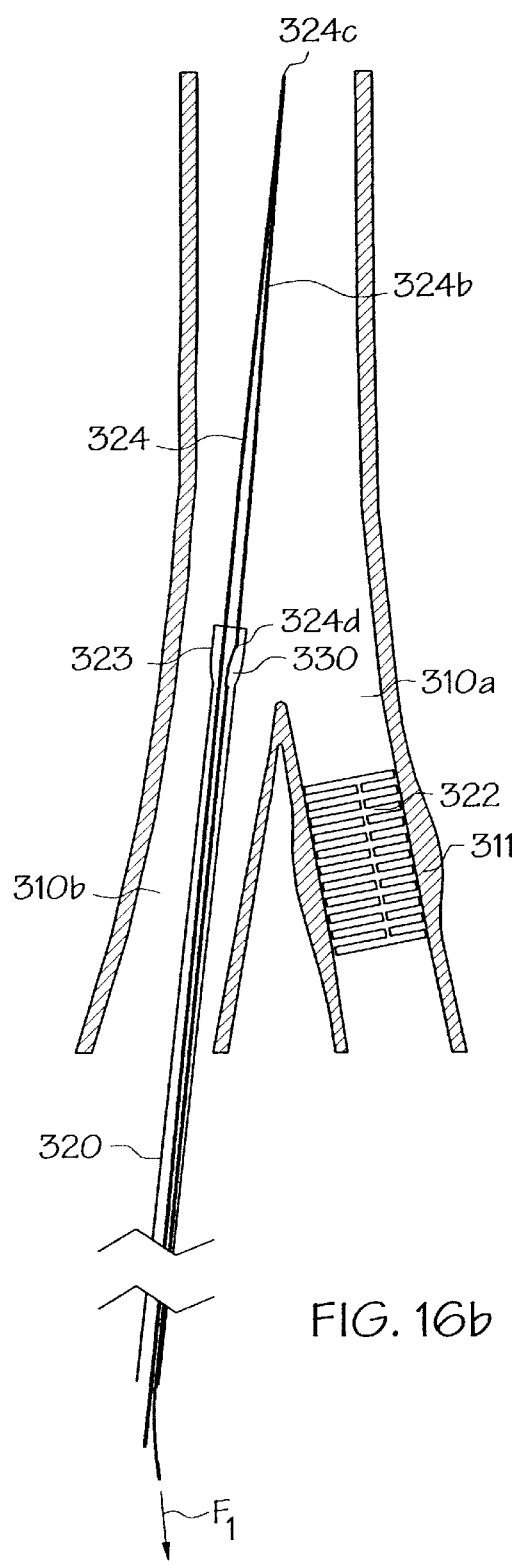
FIG. 16b shows the use of the pull wire to pull the distal end back into the delivery sheath once the stent has been delivered to and expanded in its desired location.

Referring now to FIG. 16a, the restraining means also play an important safety role. Catheter 320 with core wire 324, side branch wire 324b and junction point 324c is shown. The tip 324d of side branch wire 324b is connected to a thin, flexible release wire 330 that follows a shortened path from the proximal end of core wire 324, toward the junction 324c and down core wire 324 to its distal end. The release wire 330 runs inside stent 322, and is mounted without any tension force. In configurations that utilize balloon angioplasty or related elastic expansion devices, the release wire 330 would be disposed over the outer surface of the balloon (not shown), but still within the unexpanded stent. At the proximal side 310b of the body lumen 310, the pulling force $F_0$ on the core wire 324 is zero. FIG. 16b shows how catheter 320 can be removed once the stent 322 has been inserted. After angioplasty or stenting, the junction point 324c is moved distally until the tip 324d of the side branch wire 324b moves beyond the bifurcation point 312c of the body lumen 310. In order to bring side branch wire 324b and core wire 324 in their parallel position, the operator pulls at the proximal end of the release wire 330 with a force $F_1$, while core wire 324 is held still, thus forcing tip 324d of side branch wire 324b to move closer to core wire 324 and finally into delivery sheath 323. Then the whole device can easily be removed through the side branch 310b of the bifurcating lumen 310. As with the embodiment shown in FIGS. 15a–15f, the core wire 324 can be of hollow tubular construction such that a fluid supply line (not shown) could be disposed inside, thus integrating with a balloon-expandable stent. In another variation, the release wire 330 could be disposed within core wire 324 when the latter is in the aforementioned hollow tubular configuration.

Other modifications of this invention beyond these embodiments specifically described here may be made without departing from the spirit of the invention. Accordingly, such modifications are considered within the scope of the invention as limited solely by the appended claims.

What is claimed is:

1. A catheter configured for the placement of a bifurcated surgical device in a body lumen such that only a single surgical incision is necessary, said catheter comprising:
    an elongate body of substantially tubular construction, said elongate body comprising:
        a proximal end;
        a distal end sufficiently enlarged relative to said proximal end so as to sheath engaging end portions of said bifurcating surgical device; and
        a hollow core extending from said proximal end to said distal end; and
    a central catheter wire disposed substantially within and translatable relative to said hollow core of said elongate body such that said central catheter wire can deploy said bifurcated surgical device relative to said catheter, said central catheter wire comprising:
        a first leg portion with a user-engageable proximal end and a distal end, said first leg portion configured to engage a first branch section of said bifurcated surgical device;
        a second leg portion with a distal end coupled to said distal end of said first leg portion at a bifurcation point; said second leg portion configured to engage a second branch section of said bifurcated surgical device; and
        a trunk portion with a proximal end coupled to said first leg portion and said second leg portion at said bifurcation point, said trunk portion configured to engage a trunk section of said bifurcated surgical device.

2. A catheter according to claim 1, wherein said central catheter wire is biased such that said first leg portion, said second leg portion and said trunk are substantially parallel.

3. A catheter according to claim 1, further comprising:
    a first marker disposed at said proximal end of said elongate body; and
    a second marker disposed at said user engageable proximal end of said first leg portion such that the relative axial and angular positions between said first and second leg portions provide indicia of the translational and angular orientations of said surgical device relative to said body lumen.

4. A catheter according to claim 1, further comprising:
    a plurality of travelling sheaths, each configured to restrain a portion of said bifurcated surgical device encased therein; and
    a travelling sheath deployment wire disposed adjacent said central catheter wire, said travelling sheath deployment wire coupled to at least one of said plurality of travelling sheaths.

5. A catheter according to claim 4, wherein said central catheter wire further includes at least one mechanical stop disposed thereon.

6. A catheter according to claim 4, wherein said plurality of travelling sheaths are configured to be decoupled from one another.

7. A method for implanting a bifurcated surgical device having first and second branch sections connected to a trunk in such a way that said branch sections are resiliently biased to open to a preferred angle between them, said method comprising the steps of:
    defining a delivery catheter to include:
        an elongate body of substantially tubular construction, said elongate body comprising:
            a proximal end;
            a substantially hollow distal end sufficiently enlarged relative to said proximal end so as to define a restraining means; and
            a hollow core extending from said proximal end to said distal end; and
        a central catheter core wire disposed within and positionable relative to said hollow core of said elongate body, said central catheter wire comprising:
            a first leg portion with a proximal end and a distal end;
            a second leg portion with a distal end coupled to said distal end of said first leg portion at a wire bifurcation point;
            a trunk portion with a proximal end coupled to said first leg portion and said second leg portion at said wire bifurcation point;
    attaching said bifurcated surgical device to at least a portion of said delivery catheter;
    placing at least an end of said branch sections of said bifurcated surgical device in said restraining means such that said branch sections and trunk are substantially parallel;
    routing said surgical device and said distal end of said catheter into a body lumen bifurcating point in such a position that both of said branch sections of said surgical device are positioned entirely beyond said body lumen bifurcation point, where said body lumen bifurcation point includes a trunk section and branch sections;
    releasing said branch sections of said bifurcated surgical device from said restraining means to enable them to occupy said preferred angle relative to one another;
    seating said bifurcated surgical device adjacent said body lumen bifurcation point such that each of said trunk and branch sections of said bifurcated surgical device are in operative cooperation with respective said trunk and branch sections of said body lumen;

causing said branch and trunk sections of said bifurcated surgical device to expand until they come in the desired final size in their respective said trunk and branch sections of said body lumen;

reducing contact between said delivery catheter and said bifurcated surgical device, thereby effecting return of said delivery catheter to a substantially as-inserted dimension;

moving said delivery catheter without said bifurcated surgical device to a position where said leg portions of said delivery catheter can elastically return to a preferable, substantially parallel state;

moving said restraining means over at least a portion of said first and second leg portions to secure said delivery catheter in said substantially parallel state; and removing said delivery catheter from the patient's body.

8. The method according to claim 7 wherein the bias between said branch sections of said bifurcated surgical device is sufficient to overcome a contrariwise tendency to return to said substantially parallel state for said leg portions of said delivery catheter.

9. The method according to claim 7, wherein said bias between said branch sections of said bifurcated surgical device is caused by elastic energy which is stored in at least one of said bifurcated surgical device, an additional elastic backbone element defining at least a part of said surgical device, or an attached graft material.

10. The method according to claim 7, wherein said step of causing said trunk and branch sections of said bifurcated surgical device to expand is performed by inflating bifurcated balloon sections that are mounted on said central catheter wire, and inside said respective trunk and branch sections.

11. The method according to claim 10, said method including the step of deflating said balloon sections after placement of said bifurcated surgical device in said body lumen.

12. The method according to claim 11, wherein said inflation and deflation of said balloon sections is performed by moving a fluid through said hollow core of said elongate body.

13. The method according to claim 12, wherein the time of deflation and the final diameter for said balloon sections are minimized by surrounding said balloon sections with an elastic biasing sleeve that squeezes said fluid out of said balloon, while helping to maintain the concentric, circular cross section of said deflating balloon sections.

14. The method according to claim 7, wherein the step of causing said trunk and branch sections of said bifurcated surgical device to expand is performed by axial release of a plurality of travelling sheaths, each of said plurality of travelling sheaths configured to hold respective said trunk and branch sections in their compressed state.

15. The method according to claim 14, wherein a travelling sheath deployment wire is connected to the free end of at least one of said plurality of travelling sheaths, and is used to push or pull said at least one travelling sheath from its respective bifurcated surgical device trunk or leg portion.

16. The method according to claim 15, wherein the release of said bifurcated surgical device portions from said travelling sheaths is caused by a series of axial movements of said travelling sheath deployment the wire in proximal and distal direction while said bifurcated surgical device is in a constant axial position relative to the body lumen.

17. The method according to claim 16, wherein said travelling sheath deployment wire includes a mechanical stop at its proximal end, and said central catheter wire includes at least one mechanical stop such that it can apply an axial force to one of said plurality of travelling sheaths in response to user-applied force.

18. The method according to claim 14, wherein the step of minimizing the dimensions of the delivery catheter after expansion of said bifurcated surgical device sections is performed by the use of an elastic biasing sleeve, surrounding at least one of said plurality of travelling sheaths.

19. The method according to claim 7, wherein said elongate body includes enhanced flexibility to facilitate movement through said body lumen.

20. The method according to claim 19, wherein said elongate body is made of a polymer, a metal or a combination thereof.

21. The method according to claim 7, wherein said delivery catheter is made from the group of materials consisting of polymers, metals, memory materials with superelastic or temperature-dependent behavior, organic materials, ceramics, or combinations thereof.

22. The method according to claim 7, wherein at least one marker disposed on a proximal end of said central catheter wire provides angular position indicia of said bifurcated surgical device as well as relative axial position of said components within said delivery catheter.

23. The method according to claim 7, wherein said bifurcated surgical device is an angioplasty balloon.

24. The method according to claim 7, wherein said bifurcated surgical device is a stent comprising a graft.

* * * * *